United States Patent [19]

Horton et al.

[11] Patent Number: 5,478,861
[45] Date of Patent: Dec. 26, 1995

[54] CYTOTOXIC MACROLIDES AND METHODS OF USE

[75] Inventors: Paul A. Horton, Vero Beach; Frank Koehn, Fort Pierce; Ross E. Longley; Oliver J. McConnell, both of Vero Beach; Shirley A. Pomponi, Fort Pierce, all of Fla.

[73] Assignee: Harbor Branch Oceanographic Institution, Inc., Fort Pierce, Fla.

[21] Appl. No.: 198,747

[22] Filed: Feb. 18, 1994

[51] Int. Cl.$^6$ .................................................. A61K 31/335
[52] U.S. Cl. ................................................ 514/450; 549/267
[58] Field of Search ............................ 549/267; 514/450

[56] References Cited

U.S. PATENT DOCUMENTS

| | | | |
|---|---|---|---|
| 3,697,547 | 10/1972 | Kurath et al. | 549/267 |
| 4,164,584 | 8/1979 | Kupchan et al. | 549/267 |
| 4,548,814 | 10/1985 | Rinehart, Jr. | 530/317 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |
| 4,833,257 | 5/1989 | Pettit et al. | 549/267 |
| 4,859,782 | 8/1989 | Higa et al. | 549/267 |
| 4,873,347 | 10/1989 | Hammann et al. | 549/267 |
| 4,996,229 | 2/1991 | Moore et al. | 514/450 |
| 5,096,922 | 3/1992 | Reichenbach et al. | 514/450 |
| 5,196,447 | 3/1993 | Pettit et al. | 514/450 |

OTHER PUBLICATIONS

Faulkner, D. J. (1984) "Marine Natural Products: Metabolites of Marine Invertebrates" Natural Products Reports 1:551–598.
Faulkner, D. J. (1986) "Marine Natural Products" Natural Products Reports 3:1–33.
Faulkner, D. J. (1987) "Marine Natural Products" Natural Products Reports 4:539–576.
Uemura, D. et al. (1985) "Norhalichondrin A: An Antitumor Polyether Macrolide from a Marine Sponge" J. Am. Chem. Soc. 107:4796–4798.

Primary Examiner—C. Warren Ivy
Assistant Examiner—Amelia Owens
Attorney, Agent, or Firm—Saliwanchik & Saliwanchik

[57] ABSTRACT

A novel macrolide compound, lasonolide A, has been isolated from a marine sponge. This compound, derivatives of the compound, and compositions comprising the compound or its derivatives, are useful as antitumor agents and as biochemical tools.

6 Claims, 1 Drawing Sheet

CYTOTOXIC MACROLIDES AND METHODS OF USE

BACKGROUND OF THE INVENTION

Considerable research and resources have been devoted to oncology and antitumor measures including chemotherapy. While certain methods and chemical compositions have been developed which aid in inhibiting, remitting, or controlling the growth of tumors, new methods and antitumor chemical compositions are needed. It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge *Theonella sp.*; and U.S. Pat. No. 4,737,510 discloses compounds, having antiviral and antibacterial properties, isolated from the Caribbean sponge *Agelas conifedn*. Clearly, marine sponges have proved to be a source of biological compounds, and a number of publications have issued disclosing organic compounds derived from marine sponges, including Scheuer, P. J. (ed.) *Marine Natural Products, Chemical and Biological Perspectives*, Academic Press, New York, 1978–1983, Vol. I-V; Faulkner, D. J., (1984) Natural Products Reports 1:551–598; Natural Products Reports (1986) 3:1–33; Natural Products Reports (1987) 4:539–576; J. Am. Chem. Soc. (1985) 107:4796–4798.

The present invention, utilizing sponges as a source material, has provided the art with a class of biologically active compounds heretofore not described in the art and new pharmaceutical compositions comprising those compounds which are useful as antitumor agents. Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The subject invention concerns novel compounds, macrolides, and methods of use for these compounds. The structures for the subject macrolides, Compounds (I)–(VIII), are shown below. The macrolide compounds have biological activity and can be effective to control cell proliferation. Specifically exemplified herein is lasonolide A, which was isolated from a Forcepia sponge. Lasonolide A is a specific derivative of Compound (I), disclosed herein below, wherein $R_1$ is OH and $R_2$ is $CH_2OH$. The structure of lasonolide A is shown by the following chemical formula:

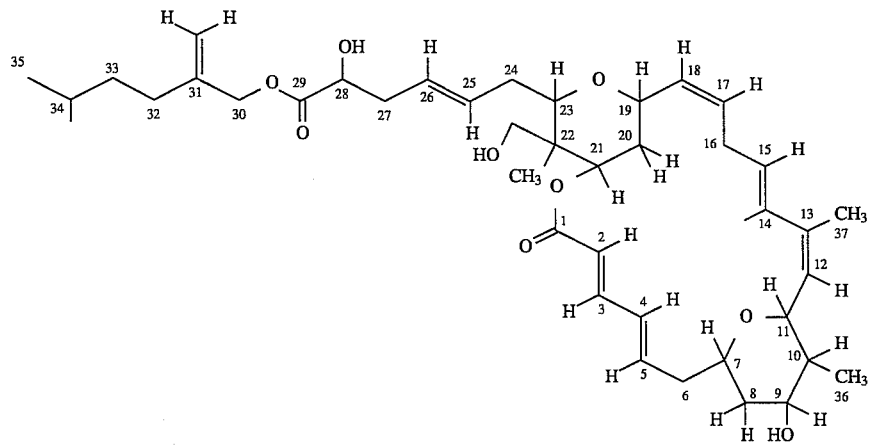

Lasonolide A has been found to inhibit tumor cell growth. This compound and derivatives and analogs thereof are therefore useful in the treatment of cancer in animals and humans.

The compounds of the subject invention can also be used as a biochemical probe in determining various aspects of cytoskeletal changes in cells, including cancer and normal cells, and therefore can be useful as an important tool in the research of certain diseases of plants, animals, and humans.

DETAILED DISCLOSURE OF THE INVENTION

Figure 1:
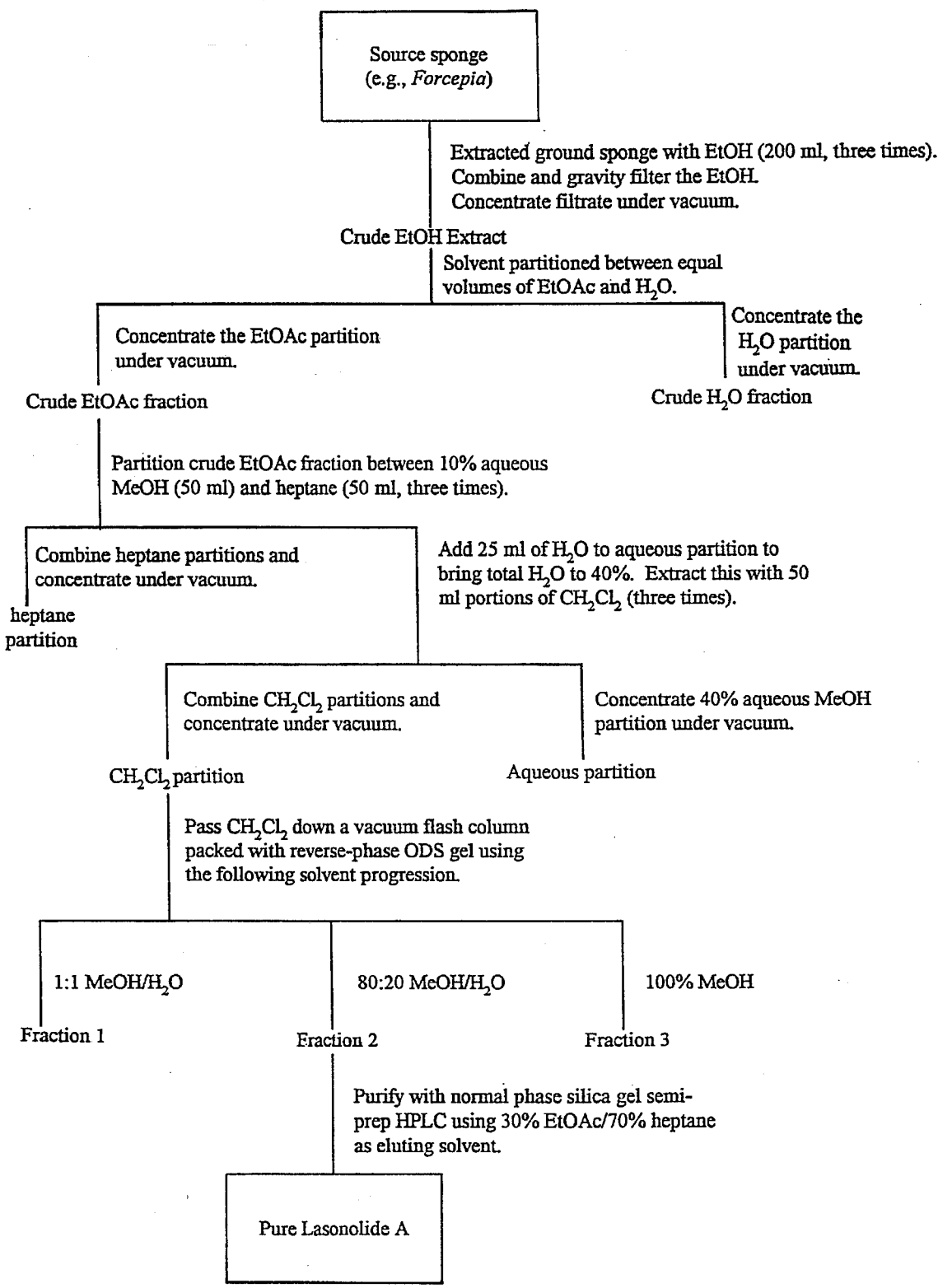
FIG. 1 depicts a scheme for preparing lasonolide A.

The subject invention pertains to a novel chemical compound which can be isolated from marine sponges. Analogs and derivatives of this compound are also described and claimed. These compounds have been shown to possess antitumor activity. Thus, the subject invention pertains to the compounds themselves, as well as pharmaceutical compositions containing these compounds. Also disclosed and claimed are methods for administering the novel compositions. The analogs and derivatives of these compounds can be produced by known procedures. The parent compound can be isolated from marine sponges as described below.

The isolation of the natural product, lasonolide A, was performed using solvent partitioning techniques followed by chromatography. The final purification of the novel compound can be achieved either by crystallization or by using high performance liquid chromatography (HPLC). The structure of lasonolide A was determined mainly on the basis of its $^1$H and $^3$C NMR data, and is represented by the following chemical formula:

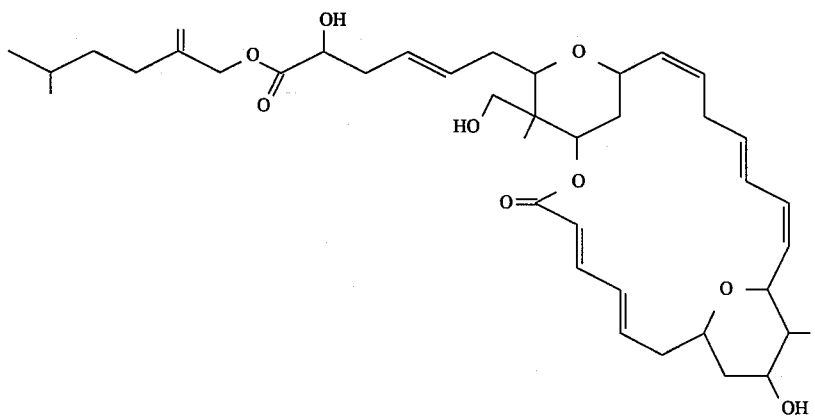

A preferred embodiment of the subject invention is lasonolide A, which comprises the structure of Compound (I):

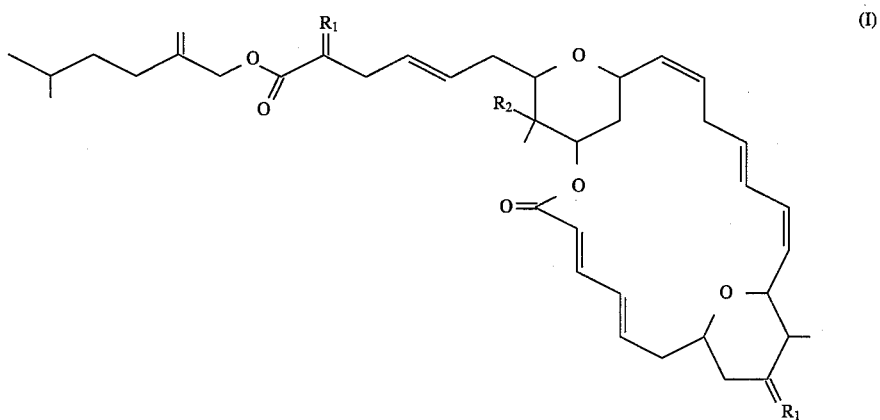

wherein the R groups for the specific lasonolide A compound are defined as follows:

$R_1$=H and OH; and $R_2$=CH$_2$OH.

Other embodiments or analogs of lasonolide A comprise the structure where $R_1$=O, or H and OH, or H and OR, where
R is H, acyl, alkyl, or phenyl; and $R_2$=alkyl, H, CH$_2$OH, CH$_2$OR, CHO, COOH, COOR', or COO$^-$X$^+$, where X=H, Na, K, amines, or other monovalent cationic molecule;

R=acyl, alkyl, or phenyl; and R'=alkyl or phenyl.

Other compounds of the subject invention are embodied by Compounds (II)–(VIII). Specifically, Compound (II) has the structure:

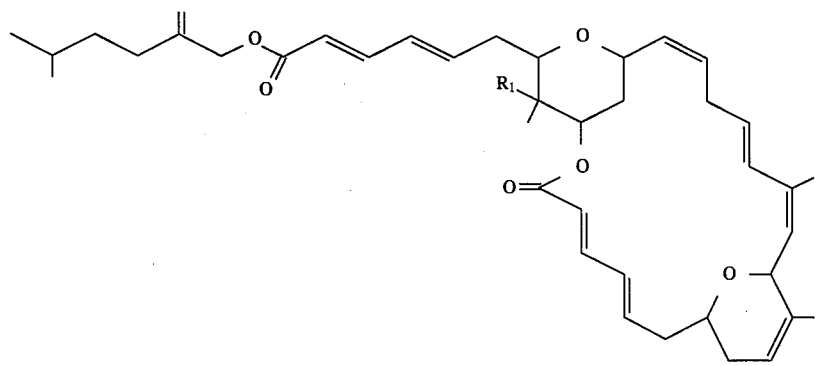

(II)

wherein $R_1$=H, alkyl, $CH_2OR$, CHO, COOR', or $COO^-X^+$, where X is H, Na, K, amine, or other monovalent cationic molecule;

R is H, acyl, alkyl, or phenyl; and

R' is H, alkyl, phenyl.

A preferred compound according to the structure of Compound (II) is where $R_1$=$CH_2OH$.

Compound (III) has the structure:

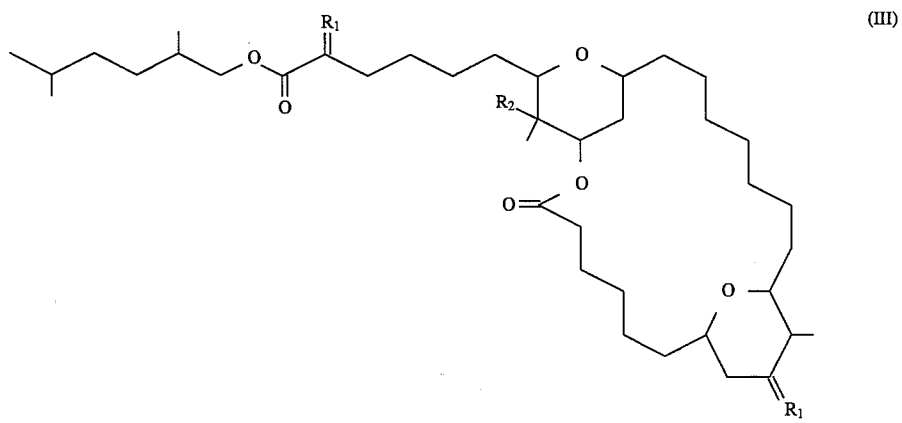

(III)

wherein $R_1$=O, or H and OH, or H and OR; $R_2$ is H, alkyl, $CH_2OR$, CHO, COOR', or $COO^-X^+$, where X is H, Na, K, amine, or other monovalent cationic molecule;

R is H, acyl, alkyl, or phenyl; and

R' is H, alkyl, or phenyl.

A preferred compound according to the structure of Compound (III) is where $R_1$=H and OH, and $R_2$=$CH_2OH$.

Compound (IV) has the structure:

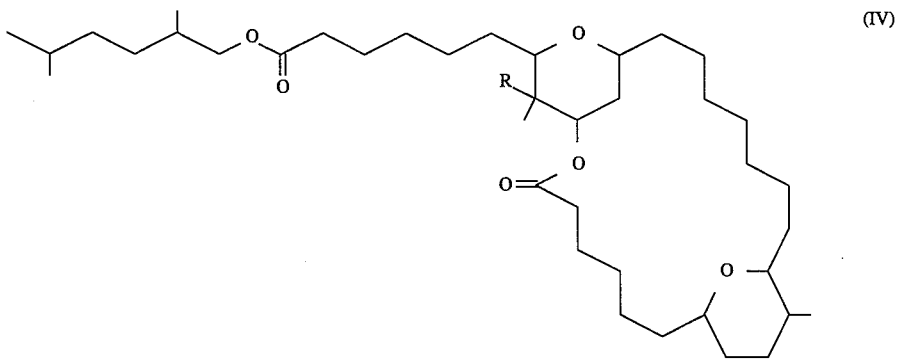

(IV)

wherein

R is H, alkyl, $CH_2OR'$, CHO, COOR", or $COO^-X^+$, where X is H, Na, K, amine, or other monovalent cationic molecule;

R' is H, acyl, alkyl, or phenyl; and
R" is H, alkyl, or phenyl.

A preferred compound according to the structure of Compound (IV) is where R=CH$_2$OH.

Compound (V) has the structure:

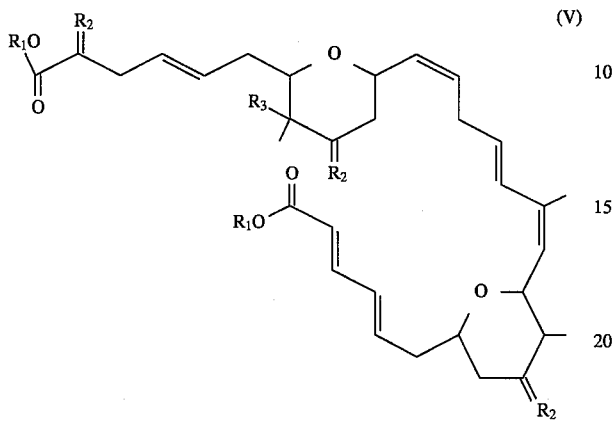

(V)

wherein
- R$_1$=H, R, or X, where
  - X is Na, K, amine, or other monovalent cationic molecule;
  - R is H, acyl, alkyl, or phenyl;
- R$_2$=O, or H and OH, or H and OR, where
  - R is H, acyl, alkyl, or phenyl; and
- R$_3$=H, alkyl, CH$_2$OR, CHO, COOR', or COO$^-$X$^+$, where
  - X is H, Na, K, amine, or other monovalent cationic molecule;
  - R is H, acyl, alkyl, or phenyl; and
  - R' is alkyl or phenyl.

Compound (VI) has the structure:

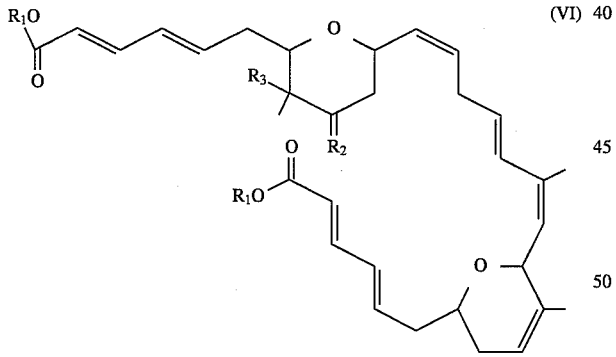

(VI)

wherein
- R$_1$=H, R, or X where
  - X is Na, K, amine, or other monovalent cationic molecule; and
  - R is alkyl or phenyl;
- R$_2$=O, or H and OH, or H and OR, where
  - R is H, acyl, alkyl, or phenyl;
- R$_3$=H, alkyl, CH$_2$OH, CH$_2$OR, CHO, COOH, COOR', COO$^-$X$^+$, where
  - X is Na, K, amine, or other monovalent cationic molecule;
  - R is acyl, alkyl, or phenyl; and
  - R' is alkyl or phenyl.

Compound (VII) has the structure:

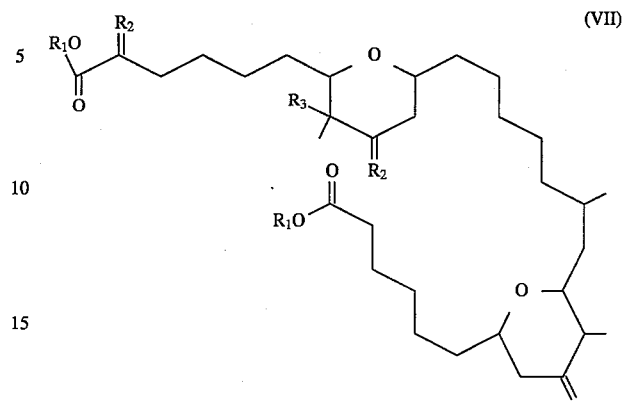

(VII)

wherein
- R$_1$=H, R, or X, where
  - X is Na, K, amine, or other monovalent cationic molecule; and
  - R is alkyl or phenyl;
- R$_2$=O, or H and OH or OR, where
  - R is H, acyl, alkyl, or phenyl;
- R$_3$=H, alkyl, CH$_2$OH, CH$_2$OR, CHO, COOH, COOR', COO$^-$X$^+$, where
  - X is Na, K, or amine; R is acyl, alkyl, or phenyl; and
  - R' is alkyl or phenyl.

Compound (VIII) has the structure:

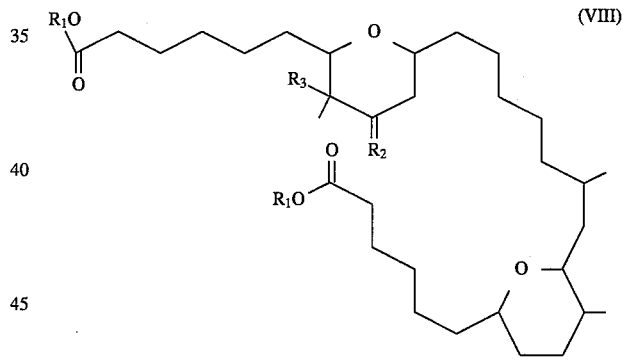

(VIII)

wherein
- R$_1$=H, R, or X, where
  - X is Na, K, amine, or other monovalent cationic molecule; and
  - R is alkyl or phenyl;
- R$_2$=O, H and OH, H or OR, where
  - R is H, acyl, alkyl, or phenyl;
- R$_3$=H, alkyl, CH$_2$OH, CH$_2$OR, CHO, COOH, COOR', COO$^-$X$^+$, where
  - X is Na, K, or amine; R is acyl, alkyl, or phenyl; and
  - R' is alkyl or phenyl.

All embodiments and derivatives of lasonolide A can be prepared by using standard reactions and procedures which are well known to those skilled in the art. For example, derivatives of lasonolide A which are prepared by replacing R with an acetyl (Ac) group can be achieved via standard acetylation reactions. The specific reactions are described in more detail below. See Example 6—Analogs and Variants of the Compounds.

The compound lasonolide A has not previously been isolated from a natural source. The subject compounds can be isolated from a sponge in the genus Forcepia. In addition to Forcepia, other sponges can also be used as a source for the subject Compounds (I)–(VIII). These other sponges include Acarnus, Lissodendoryx, Hernitedania, Tedania, and the like. The compounds of the subject invention, including derivatives thereof, have antitumor properties. Thus, they can be used for the treatment of a number of diseases including cancer. In addition, the subject compounds can be used as biochemical probes, i.e., useful tools in the study of the cytoskeletal structure of plant, animal, and human cells.

Following are examples which illustrate procedures, including the best mode, for practicing the invention. These examples should not be construed as limiting. All percentages are by weight and all solvent mixture proportions are by volume unless otherwise noted.

EXAMPLE 1—IDENTIFICATION AND LOCATION OF MARINE SPONGE

The sponge of interest, Forcepia sp. (order Poecilosclerida, Family Myxillidae), can be collected off the North Shore, Grand Ghut, north of East Point of Guana Island, British Virgin Islands (Lat. 18 29.13° N., long. 64 37.65° N.) at a depth of 63 feet. The topography of the collection site is smooth pavement rock and sand. The sponge is red-orange in color and is spherical in shape. This species of Forcepia was identified as ? trilabis species. See Van Soest, R. W. M. (1984) "Marine sponges from Curacao and other Caribbean localities, Part III. Poecilosclerida," *Stud. Fauna Curacao Caribb. Isl.* 66(199):1–167. The sponge has been classified as follows:

| | |
|---|---|
| Phylum: | Porifera |
| Class: | Demospongiae |
| Order: | Poecilosclerida |
| Family: | Myxillidae |
| Genus: | Forcepia |
| Species: | ?trilabis |

EXAMPLE 2—ISOLATION OF LASONOLIDE A

To obtain the subject compound, lasonolide A, the source sponge of the subject compounds, *Forcepia ? trilabis*, was ground in a blender and extracted with three 200 ml portions of ethanol. Extraction times were of approximately 8, 15, and 8 hours, respectively. The ethanol extracts were decanted from the ground sponge, gravity filtered, combined and concentrated under vacuum yielding a crude ethanol extract. This extract was then solvent partitioned between equal volumes of water and ethyl acetate. The ethyl acetate partition was concentrated under vacuum and further solvent partitioned between heptane and 10% aqueous methanol. Sufficient water was added to the aqueous partition to bring the total water content to 40%. The 40% aqueous methanol fraction was then partitioned with methylene chloride. The methylene chloride partition was then concentrated under vacuum and further purified by passing it down a vacuum flash column (VFC) packed with reverse-phase ODS gel using a solvent gradient of 1:1 methanol/water, 80:20 methanol/water and 100% methanol. The fraction obtained from 80:20 methanol/water was then purified by HPLC using a normal-phase silica gel semi-prep column and 70:30 ethyl acetate/heptane as the eluting solvent. This yielded pure lasonohde A. A schematic representation of the isolation procedure is shown in FIG. 1. Analogs and derivatives of the subject compounds can be obtained using substantially similar extraction and purification techniques.

The bioactive compound, lasonolide A, is the major cytotoxic compound present in the organism and can be isolated in pure form with about 0.05% yield with respect to the wet weight of the sponge. Large scale isolation can be done by using RP-18 vacuum liquid chromatography on the water extract (which can be obtained after partitioning the methanol extract with water/ethyl acetate) followed by RP-18 HPLC on a preparative column. All the necessary material for this process is readily available to a person skilled in this art.

EXAMPLE 3—CHARACTERIZATION OF COMPOUND

Characterization of lasonolide A was determined by NMR spectral analysis. The results of these data are shown in Table 1, below.

TABLE 1

| | NMR data for lasonolide A. | | | | |
|---|---|---|---|---|---|
| Position | $^1H^a$ | $^{13}C^{b,c}$ | Position | $^1H^a$ | $^{13}C^{b,c}$ |
| 1 | | 168.5 (s) | 21 | 4.97 (s) | 74.1 (d) |
| 2 | 5.71 (d, J=15.3) | 118.4 (d) | 22 | | 41.3 (s) |
| 3 | 7.24 (dd, J=15.5, 10.8) | 148.3 (d) | 23 | 3.57 (dd, J=10.8, 2.7) | 78.0 (d) |
| 4 | 6.27 (dd, J=15.3, 11.0) | 129.0 (d) | 24 | 2.20 (m) 2.06 (m) | 28.0 (t) |
| 5 | 6.15 (dt, J=15.3, 6.0) | 145.8 (d) | 25 | 5.69 (dd, J=18.0, 7.5) | 130.9 (d) |
| 6 | 2.36 (m) | 38.5 (t) | 26 | 5.50 (m) | 125.1 (d) |
| 7 | 4.00 (m) | 72.5 (d) | 27 | 2.52 (m) | 32.6 (t) |
| 8 | 1.69 (m) 1.55 (m) | 33.8 (t) | 28 | 4.25 (m) | 70.3 (d) |
| 9 | 4.06 (m) | 70.8 (d) | 29 | | 174.0 (s) |
| 10 | 1.66 (m) | 38.4 (d) | 30 | 4.62 (s) | 67.7 (t) |
| 11 | 4.82 (dd, J=9.1, 2.1) | 68.9 (d) | 31 | | 143.8 (s) |
| 12 | 5.46 (d, J=9.3) | 124.6 (d) | 32 | 2.07 (m) | 31.0 (t) |
| 13 | | 138.9 (s) | 33 | 1.34 (m) | 36.7 (t) |
| 14 | 6.59 (d, J=15.6) | 129.1 (d) | 34 | 1.56 (m) | 27.7 (d) |
| 15 | 5.83 (dt, J=15.8, 7.5) | 129.7 (d) | 35 | 0.90 (d, J=6.8) | $22.5 (q)^d$ |
| 16 | 2.90 (dd, J=12.3, 7.3) 2.73 (m) | 33.7 (t) | 36 | 1.06 (d, J=7.1) | 11.4 (q) |

TABLE 1-continued

NMR data for lasonolide A.

| Position | $^1H^a$ | $^{13}C^{b,c}$ | Position | $^1H^a$ | $^{13}C^{b,c}$ |
|---|---|---|---|---|---|
| 17 | 5.53 (m) | 129.0 (d) | 37 | 1.82 (s) | 21.1 (q) |
| 18 | 5.53 (m) | 134.2 (d) | 38 | 1.11 (s) | 15.2 (q) |
| 19 | 4.30 (m) | 77.1 (d) | 39 | 3.41 (d, J=11.3) 3.33 (d, J=11.3) | 65.7 (t) |
| 20 | 1.89 (dt, J=12.0, 2.5) 1.42 (dm, J=12.0) | 35.0 (t) | 40 | 5.03 (s) 4.97 (s) | 112.5 (t) |

[a]$^1H$ spectrum recorded at 500 MHz in $CDCl_3$, referenced to residual $CHCl_3$ (7.26 ppm).
[b]$^{13}C$ recorded at 90 MHz in $CDCl_3$, referenced to $CDCl_3$ (77.0 ppm).
[c]$^{13}C$ multiplicities determined by DEPT experiment.
[d]Signal represents two degenerate carbons.

EXAMPLE 4—ANTITUMOR ACTIVITY

Lasonolide A was tested for toxicity against P388 murine leukemia cells and A549 human lung carcinoma cells, and for their ability to perturb signal transduction pathways associated with activation of protein kinase C (PKC) and EL-4 cell adherence.

A. Maintenance of cell line. The P388 murine leukemia cells were obtained from Dr. J. Mayo, National Cancer Institute, Bethesda, Md. The A549 cells and EL-4.IL-2 cells (TIB) were obtained from the American Type Culture Collection, Rockville, Md. The P388 cells were maintained in Roswell Park Memorial Institute medium 1640 (RPMI-1640) supplemented with 10% horse serum and cultured in plastic tissue culture flasks and kept in an incubator at 37° C. in humidified air containing 5% $CO_2$. The A549 cells were similarly maintained in RPMI-1640 but supplemented with 10% fetal bovine serum. Antibiotic-free stock cultures of P388 and A549 cells were subcultured to los cells/ml by dilutions in fresh growth medium at 2 to 5 day intervals. The EL-4 cells were similarly maintained but supplemented with 10% v/v heat-inactivated fetal calf serum, 100 U/ml penicillin, 100 µg/ml streptomycin, 6 µg/ml L-glutamine, and $5 \times 10^{-3}$M 2-mercaptoethanol (TCM) (Grand Island Biologicals Co., Grand Island, N.Y.).

Cells were passaged every 3–4 days. Viability was determined by Trypan blue exclusion and always exceeded 80%. For the adherence assay, cells were utilized within 15 passages of frozen stock cultures. Phorbol-12-myristate-13-acetate (PMA), and 4α-phorbol-12-myristate-13-acetate (4α-PMA) were obtained from LC Services Corporation (Woburn, Mass.). Stock solutions of PMA and 4α-PMA were prepared in DMSO and were stored at −70° C. prior to use.

B. Procedure. To assess the antiprolfferative effects of agents against P388 cells, 200 µl cultures (96-well tissue culture plates, Nunc, Denmark) were established at $1 \times 10^5$ cells/ml in drug-free medium or medium containing the crude extract at a final dilution of 1:500 or intermediate and pure compounds at 10.0, 1.0, 0.10, and 0.010 µg/ml. The solvent used for all dilutions was ethanol, which was removed from all plates under vacuum. After 48 hour exposures, P388 cells were enumerated using 3-[4,5-dimethylthiazol-2-yl]-2,5-diphenyltetrazolium bromide (MTT) as described below.

To assess the antiprolfferative effects of lasonolide A or its analogs against the A549 cells, cells were established as monolayer cultures in wells of microtiter plates at a final concentration of $1.5 \times 10^5$ cells/ml of medium 24 hours prior to exposure to the compounds. A volume of 100 µl of medium was removed from each culture well and replaced with a volume of 100 µl of drug-free medium or medium containing the crude extract at a final dilution of 1:500 or intermediate and pure compounds at 10.0, 1.0, 0.10, and 0.010 µg/ml. Plates were incubated at 37° C. for 72 hours and the cells enumerated with MTF as described below.

To quantitate the effects of lasonolide A or its analogs on cell proliferation, 75 µl warm growth medium containing 5 mg/ml MTT was added to each well. Cultures were returned to the incubator and left undisturbed for 90 minutes. To spectrophotometrically quantitate formation of reduced formazan, plates were centrifuged (900 g, 5 minutes), culture fluids were removed by aspiration, and 200 µl of acidified isopropanol (2 ml concentrated HCl/L isopropanol) added per well. The absorbance of the resulting solutions was measured at 570 nm with a plate reader (MR700 Microplate Reader, Dynatech Laboratories, Chantilly, Va.). The absorbance of test wells was divided by the absorbance of drug free wells, and the concentration of the compound that resulted in 50% of the absorbance of untreated cultures ($IC_{50}$) was determined by linear regression of logic-transformed data. A linear relationship between P388 and A549 cell number and formazan production was found over the range of cell densities observed in this study.

To assess the effect of the subject compound on EL-4 cells, EL-4 cells ($2.5 \times 10^5$/well) were cultured in 96-well, flat-bottomed microtiter test plates at 37° C. with the sponge metabolites in triplicate concentrations in the presence (Plate #1) or absence (Plate #2) of PMA (16 nM final concentration). The test compounds were diluted in TCM in such a manner that the final concentration of EtOH did not exceed 1.25%. Controls consisted of cells incubated alone (negative control) and cells incubated with PMA (positive control). An additional control plate (Plate #3), consisting of EL-4.IL-2 cells and identical dilutions of compounds in the absence of PMA served as a cytotoxicity plate and was not processed for adherence as described below, but used to monitor the potential cytotoxic effect of compounds for EL-4.IL-2 cells. Incubation time was 1 hour at 37° C. Following the incubation period, Plates #1 and #2 were processed as follows: the contents of each well were removed by flicking the plates into a catch tray and placing the plates inverted onto a paper towel in order to drain and blot the remaining draining wells. To each well, a volume of 100 µl of TCM was added at room temperature and the plates placed on a rotating platform shaker (Mini-Orbital Shaker, BELLCO Biotechnology, Vineland, N.J.) at setting 5 for 4 minutes. The plates were then rotated 180° and subjected to an additional 4 minutes of shaking. The plates were removed and their contents again removed as described, blotted, TCM added to each well, and the plates placed on the rotating shaker. This process was repeated for two additional wash cycles.

Following the removal of well contents, a volume of 200 μl of TCM and 75 μl of MTT solution (2 mg/ml in TCM) was added to each well of all plates. Plates were incubated at 37° C. for an additional 4 hours. Following incubation, the contents of Plates #1 and #2 were again removed by flicking the plate into the sink and the plates blotted onto paper towels. Plate #3 was centrifuged and likewise blotted. A volume of 200 μl of iPrOH was then added to each well of all plates in order to dissolve the resulting formazan crystals. The plates were read at 570 nm using a plate reader (Microplate Autoreader, Model EL-311, BIO-TEK Instruments, Inc., Winooski, Vt.). The absorbances for each set of triplicate wells were averaged and the standard error determined. Results were expressed graphically by plotting the mean absorbance and standard error of each test well. The results were interpreted as follows:

Agonist of PKC (inducer of adherence). Compound induces adherence of EL-4.IL-2 cells in the absence of PMA (Plate #2), as evidenced by absorbance of MTT metabolized by adherent cells which is greater than that of cells incubated alone (negative control).

Antagonist of PKC (inhibitor of adherence). Compound does not induce adherence of EL-4.IL-2 cells in the absence of PMA (Plate #2), as evidenced by no absorbance of MTF. Compound inhibits adherence of EL-4.IL-2 cells in the presence of PMA (Plate #1) as evidenced by no absorbance of MTF. Compound is not cytotoxic as measured by Plate #3.

C. Results. The results of the A549, P388, and EL-4 adherence assays are shown below in Table 2. Purified lasonolide A (Vial #10319) was found to have strong inhibitory properties against mouse leukemia cells and to have an $IC_{50}$ of less than 0.01 μg/ml. Lasonolide A was also found to have an $IC_{50}$ of 0.04 μg/ml against cultured human lung carcinoma cells (A549). Inhibition was also strong for lasonolide A using the EL-4 Adherence assay. The purified compound was shown to have an $IC_{50}$ of 0.019 by EL-4 Adherence. The compound lasonolide A, or a composition derived from it, can be used for inhibiting tumors in humans or in animals.

As used in this application, the terms "analogs," "variants" and "derivatives" refer to compounds which are substantially the same as another compound but which may have been modified by, for example, adding additional amino acids or side groups. The terms "analogs," "variants" and "derivatives" as used in this application also may refer to compounds which are substantially the same as another compound but which have atomic or molecular substitutions at certain locations in the compound.

As described, a preferred embodiment of the compound is lasonolide A, which comprises the structure shown above, wherein $R_1$=OH and $R_2$=CH$_2$OH. However, analogs or derivatives of this preferred embodiment can be readily prepared using commonly known, standard reactions. These standard reactions include, but are not limited to, methylation, acetylation, and acidification reactions. The derivatives and analogs specifically exemplified herein can be prepared as follows:

1. Methylation. Lasonolide A can be methylated using standard methylation procedures. For example, a methylating reagent, e.g., dimethyl sulfate, reacted with a solution of lasonolide A in methanol yields the structure shown above, wherein $R_1$=CH$_3$.

2. Acetylation. Acetyl (Ac) groups can be added to lasonolide A using a standard acetylation reaction. Acetylation can occur at a position where a free hydroxyl group is present on the molecule. For example, acetylation of lasonolide A can be carried out with excess acetic anhydride and pyridine (1:2), which will yield the structure shown above as Compound (I), wherein $R_1$ and $R_2$=CH$_2$COO$^-$. This structure can be further methylated by standard methylation procedures, as described above, and will yield the structure shown above, wherein $R_1$ and $R_2$=CH$_2$COOCH$_3$.

The subject invention embraces the specific structures shown for the compound and other compositions which are specifically exemplified. The subject invention further embraces analogs, variants, and derivatives of the structure, as well as analogs and variants of the derivatives. These analogs, variants, and derivatives are embraced within the subject invention so long as the analog, variant, or derivative

TABLE 2

Bioactivity Test Results

| A549 | | | P388 | | |
|---|---|---|---|---|---|
| Vial # | Assay # | $IC_{50}$(μg/ml) | Vial # | Assay # | $IC_{50}$(μg/ml) |
| 10319 | 123 | ND | 10319 | 130 | 0.002 |
|  | 124 | 0.04 |  | 131 | ND |

EL-4 Adherence

| Vial # | Assay # | 25 μg/ml | 12.5 μg/ml | 6.25 μg/ml | 3.125 μg/ml | $IC_{50}$(μg/ml) |
|---|---|---|---|---|---|---|
| 10319 | 37 | Inh | Inh | Inh | Inh | NA |
|  | 38 | Inh | Inh | Inh | Inh | 0.019 |

Inh = inhibition
NA = not applicable
ND = not detectable

EXAMPLE 6—ANALOGS AND VARIANTS OF THE COMPOUND

Modifications of the novel compound, lasonolide A, can readily be made by those skilled in the art.

retains substantially the same relevant biological activity as the originally exemplified compound. For example, it is well within the skill of a person trained in this art to make atomic or molecular substitutions. To the extent that these substitutions do not substantially alter the relevant biological or chemical activity, then the resulting compounds fall within the scope of the subject invention. The term "relevant biological or chemical activity" refers to the activity of interest for a particular application of a compound. For example, more than one use of lasonolide A is discussed herein. These uses include its application as a biochemical probe in cytoskeletal structure studies. When lasonolide A is being used in these ways, then "analogs" would refer to compounds where lasonolide A has been modified (by a molecular substitution, for example) without substantially altering the compound's ability to be used as a biochemical probe. Molecular substitutions are only one example of the type of modifications which are within the scope of the subject matter of this invention.

EXAMPLE 7—FORMULATION AND ADMINISTRATION

The compounds of the invention are useful for various non-therapeutic and therapeutic purposes. It is apparent from the testing that the compounds of the invention are effective for biochemical probes and for controlling tumor growth.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the an and are to be included within the spirit and purview of this application and the scope of the appended claims.

We claim:
1. A substantially pure macrolide compound having the formula:

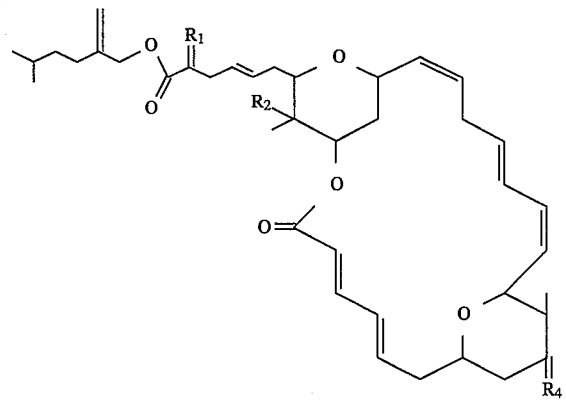

wherein
$R_1$=O, or H and OH, or H and OR, where
R is H, acyl, alkyl, or phenyl; and
$R_2$=alkyl, H, $CH_2OH$, $CH_2OR$, CHO, COOH, COOR', or $COO^-X^+$, where
X=H, Na, K, amines, or other monovalent cationic molecule;
R=acyl, alkyl, or phenyl; and R'=alkyl or phenyl.
2. The compound, according to claim 1, wherein $R_1$=H and OH; and $R_2$=$CH_2OH$.
3. A pharmaceutical composition for the inhibition of tumor cell growth comprising a compound having the formula:

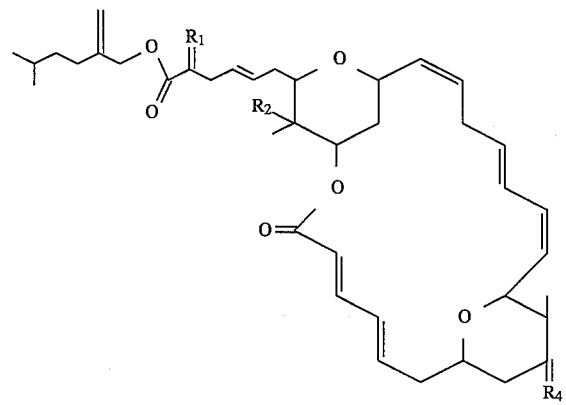

wherein
$R_1$=O, or H and OH, or H and OR, where
R is H, acyl, alkyl, or phenyl; and
$R_2$=alkyl, H, $CH_2OH$, $CH_2OR$, CHO, COOH, COOR', or $COO^-X^+$, where
X=H, Na, K, amines, or other monovalent carbonic molecule;
R=acyl, alkyl, or phenyl; and R'=alkyl or phenyl;
and a pharmaceutically acceptable carrier.
4. The pharmaceutical composition, according to claim 3, wherein $R_1$=H and OH; and $R_2$=$CH_2OH$.

5. A process for treating a human or animal hosting tumor cells, said process comprising administering to said human or animal a tumor cell-inhibiting amount of a macrolide compound having the formula:

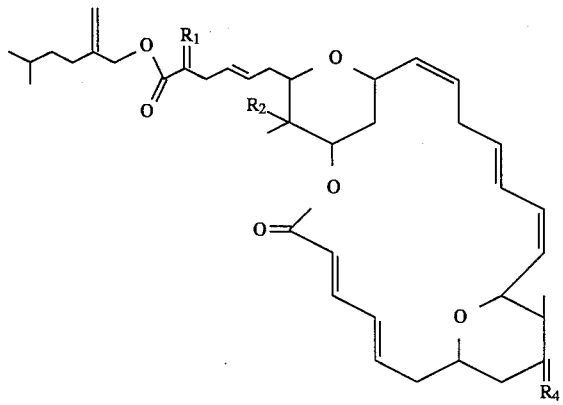

wherein $R_1$=O, or H and OH, or H and OR, where

R is H, acyl, alkyl, or phenyl; and $R_2$=alkyl, H, $CH_2OH$, $CH_2OR$, CHO, COOH, COOR', or $COO^-X^+$, where X=H, Na, K, amines, or other monovalent cationic molecule;

R=acyl, alkyl, or phenyl; and R'=alkyl or phenyl.

6. The process, according to claim 5, wherein $R_1$=H and OH; and $R_2$=$CH_2OH$.

* * * * *

UNITED STATES PATENT AND TRADEMARK OFFICE
CERTIFICATE OF CORRECTION

PATENT NO. : 5,478,861        Page 1 of 3
DATED     : December 26, 1995
INVENTOR(S) : Paul A. Horton, et al It is certified that error appears in the above-indentified patent and that said Letters Patent is hereby corrected as shown below:

Column 1: After the title: omitted should read --This invention was made with government support under NIH Grant No. NIH/NCI5R01-CA55662-03. The government has certain rights in this invention.--; line 47: "*Agelas conifedn*" should read --*Agelas coniferin*--.

Column 3: line 1: "$^3$C NMR" should read --$^{13}$C NMR--; line 3 (first structure):

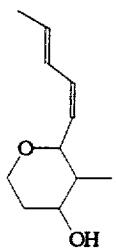   should read   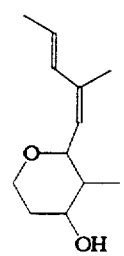

middle of page (2nd structure:)

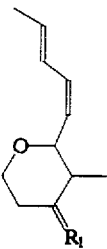   should read   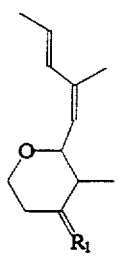

UNITED STATES PATENT AND TRADEMARK OFFICE
CERTIFICATE OF CORRECTION

PATENT NO. : 5,478,861
DATED : December 26, 1995
INVENTOR(S) : Paul A. Horton, et al It is certified that error appears in the above-indentified patent and that said Letters Patent is hereby corrected as shown below:

Column 5:   middle of page (Structure III):

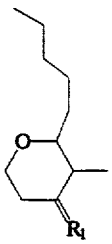   should read   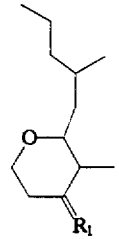

end of page (Structure IV):

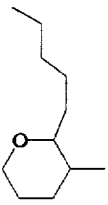   should read   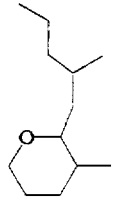

Column 10:  line 24: "lasonohde A" should read --lasonolide A--.
Column 11:  line 34: "los cells/ml" should read --$10^5$ cells/ml --; line 51: "antiprolfferative" should read --antiproliferative--; line 62: "antiprolfferative" should read --antiproliferative--
Column 12:  line 21: "MTF" should read --MTT--; lines 36-37: "logic-transformed" should read --logit-transformed--.

UNITED STATES PATENT AND TRADEMARK OFFICE
CERTIFICATE OF CORRECTION

PATENT NO. : 5,478,861  Page 3 of 3
DATED : December 26, 1995
INVENTOR(S) : Paul A. Horton, et al It is certified that error appears in the above-indentified patent and that said Letters Patent is hereby corrected as shown below:

Column 13: line 25: "MTF" should read -- MTT --; "MTF" should read -- MTT --.
Column 15: line 64: "skilled in the an" should read -- skilled in the art --.
Column 16: line 61: "carbonic" should read -- cationic --.
Column 17: line 20:

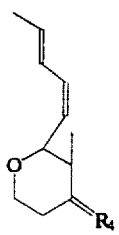 should read 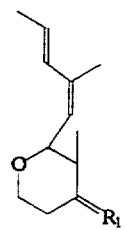

Signed and Sealed this

Seventeenth Day of September, 1996

Attest:

BRUCE LEHMAN

Attesting Officer    Commissioner of Patents and Trademarks